United States Patent [19]

Summers, Jr.

[11] Patent Number: 4,623,661
[45] Date of Patent: Nov. 18, 1986

[54] LIPOXYGENASE INHIBITING COMPOUNDS

[75] Inventor: James B. Summers, Jr., Libertyville, Ill.

[73] Assignee: Abbott Laboratories, North Chicago, Ill.

[21] Appl. No.: 727,934

[22] Filed: Apr. 26, 1985

[51] Int. Cl.$^4$ .................... C07C 83/10; A61K 31/185; A61K 31/205

[52] U.S. Cl. .......................... 514/575; 260/500.5 H; 260/501.1; 260/501.15; 514/555

[58] Field of Search ...................... 260/500.5 H, 501.1, 260/501.15; 514/575, 555

[56] References Cited

U.S. PATENT DOCUMENTS

| | | | |
|---|---|---|---|
| 3,268,542 | 8/1966 | Burk et al. | 200/500.5 H |
| 3,507,900 | 4/1970 | Burk et al. | 260/500.5 H |
| 3,560,518 | 2/1971 | Burk et al. | 260/500.5 H |
| 3,565,944 | 2/1971 | Lee et al. | 260/500.5 H |
| 3,681,445 | 8/1972 | Ruyle et al. | 260/500.5 H |
| 3,859,299 | 1/1975 | Hocker et al. | 260/500.5 H |
| 4,109,013 | 8/1978 | Grill et al. | 514/575 |

FOREIGN PATENT DOCUMENTS 303450 11/1985 European Pat. Off. .

*Primary Examiner*—J. E. Evans
*Attorney, Agent, or Firm*—Robert W. Stevenson; Martin L. Katz; Michael J. Roth

[57] ABSTRACT

Compounds of the formula

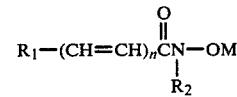

where $R_1$ is a trinuclear aromatic or biaryl group; $R_2$ is hydrogen or $C_1$ to $C_6$ alkyl or cycloalkyl; n is 0 or 1; and M is a pharmaceutically acceptable cation, are potent inhibitors of the enzymes 5-, 12-, and 15-lipoxygenase.

13 Claims, No Drawings

LIPOXYGENASE INHIBITING COMPOUNDS

TECHNICAL FIELD

This invention relates to novel organic compounds which inhibit lipoxygenase enymes. It also relates to methods of making such compounds, and to methods of inhibiting lipoxygenase enzymes in human and animal hosts in need of such treatment.

The lipoxygenases are a family of enzymes which catalyze the oxidation of arachidonic acid. The enzyme 5-lipoxygenase converts arachidonic acid to 5-hydroperoxyeicosatetraenoic acid (5-HPETE). This is the first step in the metabolic pathway which yields 5-hydroxyeicosatetraenoic acid (5-HETE) and the leukotrienes (LTs). Similarly, 12- and 15-lipoxygenase convert arachidonic acid to 12- and 15-HPETE, respectively. Biochemical reduction of 12-HPETE leads to 12-HETE, while 15-HETE is the precursor of the class of compounds known as lipoxins.

A variety of biological effects are associated with these products of lipoxygenase activity, and many are implicated as mediators in various disease states. The C4 and D4 LTs are potent constrictors of human bronchial smooth muscle in vitro, and induce bronchoconstriction when administered as aerosols to non-asthmatic human volunteers. LTB4 and 5-HETE are potent chemotactic factors for inflammatory cells such as polymorphonuclear leukocytes. They ar also found in the synovial fluid of patients with rheumatoid arthritis. The biological activity of the LTs has been reviewed by Samuelsson, *Angew. Chem. Int. Ed. Eng.*, 21, 902 (1982), and by Green and Lambeth, *Tetrahedron*, 39, 1687 (1983), the disclosures of which are incorporated herein by reference.

The product 12-HETE has been found at high levels in the epidermal tissue of patients with psoriasis. The lipoxins have been shown to stimulate lysozomal enzyme and superoxide ion release from neutrophils.

Thus, lipoxygenase enzymes play an important role in the biosynthesis of mediators of asthma, allergy, arthritis, psoriasis, and inflammation. Blocking these enzymes interrupts the biochemical pathway involved in these disease states.

BACKGROUND ART

Relatively few compounds are known from the prior art which are inhibitors of lipoxygenase enzymes. Among the lipoxygenase inhibitors known to the art are: AA-861, a 5-lipoxygenase inhibitor, disclosed in U.S. Pat. No. 4,393,075, issued July 12, 1983 to Terao et al.; pyrazolo pyridines, which are 5-lipoxygenase inhibitors, disclosed in European Patent Application of Irikura et al., Ser. No. 121,806, published Oct. 17, 1984; arachidonyl hydroxamic acid, a 5-lipoxygenase inhibitor, disclosed in E. J. Corey et al., *J. Am. Chem. Soc.*, 106, 1503 (1984) and European Patent Application of P. H. Nelson, Ser. No. 104,468, published Apr. 4, 1984; BW755C, inhibitor of 5- and 12-lipoxygenases, disclosed in Radmark et al., *FEBS Lett.*, 110, 213 (1980); nordihydroguaiaretic acid, an inhibitor of 5- and 15-lipoxygenases, disclosed in Morris et al., *Prostaglandins*, 19, 371 (1980); REV-5901, a 5-lipoxygenase inhibitor, disclosed in Coutts, Meeting Abstract 70, *Prostaglandins and Leukotrienes* '84; alkyl quinoline N-oxides, as disclosed in the German application of Kyowa Hakko Kogyo KK, abstracted in Derwent Abstract 884-289705/47, and stated to be useful for the treatment of bronchial asthma, atopic dermatitis, inflammation, edema, hypertension, ischemic brain disease and arteriosclerosis; and benzoxaprofen, disclosed in J. Walker, *Pharm. Pharmacol.*, 31, 778 (1979).

It would be useful to have compounds which are more potent inhibitors of these enzymes. In addition, a number of compounds identified as having some lipoxygenase inhibitory activity are structurally based on highly unsaturated lipid compounds which are derivatives of arachidonic acid. Such compounds are highly susceptible to oxidation in vitro and to breakdown by conventional pathways of lipid metabolism in vivo. Thus, as well as having the desired potency, it would be desirable to have agents which are relatively simple in structure, and relatively resistant to oxidation and metabolism.

It is an object of the present invention to provide compounds which are highly potent inhibitors of lipoxygenase enzymes.

It is another object of this invention to provide compounds having structures which are simpler and more stable than prior art compounds having lipid-like structures.

It is yet another object of this invention to provide compounds which inhibit lipoxygenase activity in vivo.

These and other objects of this invention will be evident from the following disclosure.

DISCLOSURE OF THE INVENTION

The present invention provides compounds of the formula

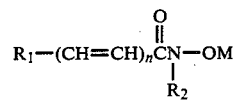

where $R_1$ is a trinuclear aromatic or biaryl group; $R_2$ is hydrogen or $C_1$ to $C_6$ alkyl or cycloalkyl; n is 0 or 1; and M is a pharmaceutically acceptable cation.

The double bonds of these compounds may have either the cis or the trans configuration, but preferably have the trans configuration.

The term "trinuclear aromatic" is used herein to refer to a substituted or unsubstituted aromatic radical having three benzene rings fused together, e.g..:

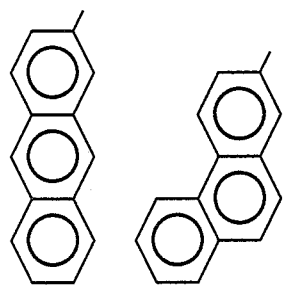

including but not limited to 1-, 2-, 3- and 9-phenanthryl, 1-, 2- and 9-anthryl and the like.

The term "biaryl group" is used herein to refer to radicals having two substituted or unsubstituted aromatic ring systems directly appended to each other:

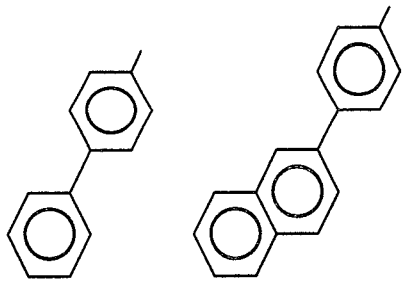

including but not limited to 2-, 3-, and 4-biphenyl, 2-, 3- and 4-(1-naphthyl)phenyl, 2-, 3- and 4-(2-naphthyl)phenyl, and the like.

The terms "alkyl" and "cycloalkyl" are used herein to mean straight and branched chain acyclic and cyclic radicals, respectively, including, but not limited to, methyl, ethyl, n-propyl, isopropyl, n-butyl, sec-butyl, isobutyl, tert-butyl, cyclopropyl, cyclohexyl, ethylcyclohexyl, and the like.

The term "pharmaceutically acceptable cation" is used herein to mean hydrogen and the nontoxic cations based on the alkali and alkaline earth metals, such as sodium, lithium, potassium, calcium, magnesium, and the like, as well as those based on nontoxic ammonium, quaternary ammonium, and amine cations, including, but not limited to, ammonium, tetramethylammonium, tetraethylammonium, methylamino, dimethylamino, trimethylamino, triethylamino, and ethylamino cations, and the like.

METHOD OF TREATMENT

This invention also provides a method of inhibiting 5-, 12- and/or 15-lipoxygenase activity in a human or lower animal host in need of such treatment, which method comprises administration to the human or lower animal host an amount of a compound of this invention effective to inhibit lipoxygenase activity in the host. The compounds of the present invention may be administered orally, parenterally or topically in dosage unit formulations containing conventional nontoxic pharmaceutically acceptable carriers, adjuvants and vehicles as desired.

The term parenteral as used herein includes subcutaneous, intravenous, intramuscular, intrathecal, intraarticular, epidural and intraarterial injection or infusion techniques, without limitation. The term "topically" encompasses administration rectally and by inhalation spray, as well as by the more common routes of the skin and the mucous membranes of the mouth and nose.

Total daily dose of the compounds of this invention administered to a host in single or divided doses may be in amounts, for example, of from 0.001 to 100 mg/kg body weight daily and more usually 0.01 to 10 mg/kg/day. Dosage unit compositions may contain such amounts or such submultiples thereof as may be used to make up the daily dose. It will be understood, however, that the specific dose level for any particular patient will depend upon a variety of factors including the activity of the specific compound employed, the age, body weight, general health, sex, diet, time and route of administration, rates of absorption and excretion, combination with other drugs and the severity of the particular disease being treated.

FORMULATION OF PHARMACEUTICAL COMPOSITIONS

This invention also provides compositions in unit dosage form for the inhibition of 5-, 12- and/or 15-lipoxygenase activity in a human or lower animal host in need of such treatment, comprising a compound of this invention and one or more nontoxic pharmaceutically acceptable carriers, adjuvants or vehicles. The amount of active ingredient that may be combined with such materials to produce a single dosage form will vary depending upon various factors, as indicated above.

A variety of materials can be used as carriers, adjuvants and vehicles in the compositions of this invention, as available in the pharmaceutical arts. Injectable preparations, such as sterile injectable aqueous or oleaginous aolutions, suspensions or emulsions, may be formulated according to known art, using suitable dispersing or wetting agents and suspending agents, as needed. The sterile injectable preparation may employ a nontoxic parenterally acceptable diluent or solvent as, for example, sterile, nonpyrogenic water or 1,3-butanediol. Among the other acceptable vehicles and solvents that may be employed are 5% dextrose injection, Ringer's injection and isotonic sodium chloride injection (as described in the USP/NF). IN addition, sterile, fixed oils are conventionally employed as solvents or suspending media. For this purpose any bland fixed oil may be used, including synthetic mono-, di- or triglycerides. Fatty acids such as oleic acid can also be used in the preparation of injectable compositions.

Suppositories for rectal administration of the compounds of this invention can be prepared by mixing the drug with suitable nonirritating excipients such as cocoa butter and polyethylene glycols, which are solid at ordinary temperatures but liquid at body temperature and which therefore melt in the rectum and release the drug.

Solid dosage forms for oral administration include capsules, tablets, pills, troches, lozenges, powders and granules. In such solid dosage forms, the active compound may be admixed with at least one inert diluent such as sucrose, lactose or starch. Such dosage forms may also comprise, as is normal practice, pharmaceutical adjuvant substances, e.g., stearate lubricating agents. In the case of capsules, tablets and pills, the dosage forms may also comprise buffering agents. Solid oral preparations can also be prepared with enteric or other coatings which modulate release of the active ingredients.

Liquid dosage forms for oral administration include pharmaceutically acceptable emulsions, solutions, suspensions, syrups and elixirs containing inert nontoxic diluents commonly used in the art, such as water and alcohol. Such compositions may also comprise adjuvants, such as wetting agents, emulsifying suspending, sweetening, flavoring and perfuming agents.

SYNTHESIS OF COMPOUNDS

The compounds of this invention in which n is 0 are synthesized according to the following scheme. Although the sequence illustrated the synthesis of compounds wherein $R_1$ is 2-phenanthryl and $R_2$ is hydrogen, other compounds of the invention can be made by substitution of the appropriate compounds for the indicated starting materials.

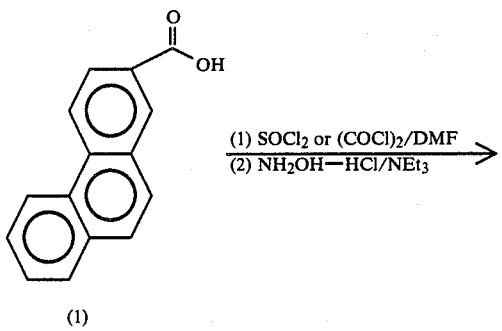

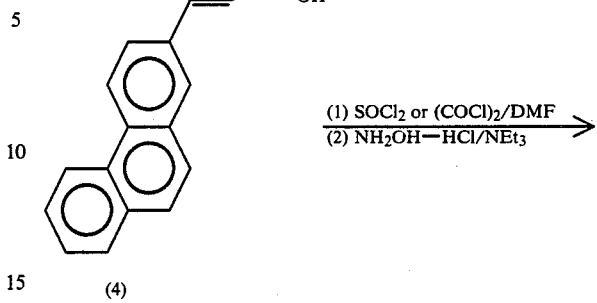

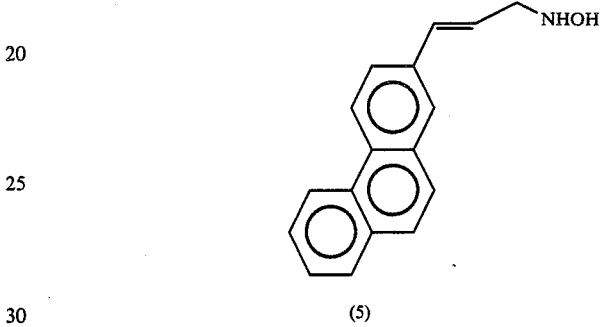

Phenanthrene carboxylic acid (1) is converted to the hydroxamic acid (2) by first treating with either thionyl chloride or oxalyl chloride followed by reaction with hydroxylamine hydrochloride in the presence of triethylamine. A mixture of tetrahydrofuran and water (2:1 v/v) is used as a solvent in the latter reaction.

Compounds in which n is 1 can be prepared by the following reaction sequence:

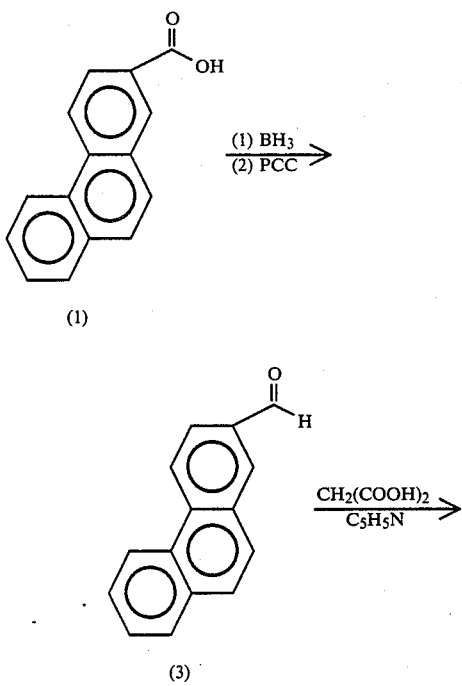

Phenanthrene acrylic acid (4) is prepared in a Doebner condensation of 2-phenanthrene carboxaldehyde (3) with malonic acid in pyridine. Phenanthrene carboxaldehyde is available from the corresponding carboxylic acid (1) by reduction with diborane and reoxidation with pyridinium chlorochromate. Acid (4) is converted to the hydroxamic acid (5) as described above.

The following examples further illustrate the synthesis and use of compounds according to this invention.

EXAMPLE 1

N-Methyl 3-(4-biphenyl)acrylohydroxamic acid a. 3-(4-biphenyl)acrylic acid

Malonic acid (6.43 g., 62 mmole) and 4-biphenyl carboxaldehyde (5.0 g., 27.5 mmole) were dissolved in pyridine (20 mL) and refluxed for 1 hour. After cooling to room temperature, the reaction mixture was poured into 2N HCl solution (200 mL). The product precipitated immediately. It was collected by filtration and recrystallized from aqueous ethanol to give colorless needles.

Melting Point: 219°–224° C.

NMR (300 MHz, DMSO-$d_6$): 6.57 (d, J=16 Hz); 7.35–7.85 (m, 10H); 12.4 (brs, 1H).

Mass Spectrum: 224, 207, 178, 165, 152.

b. N-methyl 3-(4-biphenyl)acrylohydroxamic acid

Oxalyl chloride (3.83 g, 30 mmole) was added dropwise at 0° to a solution of 3-(4-biphenyl)acrylic acid (3.0 g, 13.4 mmole) and dimethyl formamide (978 mg, 13.4 mmole) in 50 mL methylene chloride. Vigorous gas evolution was noted. After stirring for 30 minutes the above solution was added at 0° to a mixture of N-methyl hydroxylamine hydrochloride (4.45 g, 53 mmole) and triethylamine (8.12 g., 80 mmole) in THF (20 mL) and water (10 mL). After stirring for 1 hour the reaction mixture was dumped into 2N HCl solution (50 mL). The organic layer was dried with saturated sodium chloride solution and over magnesium sulfate and then the solvent was evaporated. The residue was recrystallized from acetone to give a white powder.

Melting Point: 207°–210° C.
NMR (DMSO-$d_6$): 3.25 (s, 3H); 7.25–7.8 (m, 11H); 10.15 (brs, 1H).
Mass Spectrum: 253, 237, 207, 178.

EXAMPLE 2

N-methyl-3-(3-biphenyl)-acrylohydroxamic acid

Using the method of Example 1, but using 3-biphenyl carboxaldehyde, the desired compound was obtained.
Melting Point: 133°–135° C.
NMR 300 (MHz, DMSO-$d_6$): 3.24 (s, 3H); 7.3–7.92 (m, 11H); 10.12 (brs, 1H).
Mass Spectrum: 253, 237, 207, 179, 178, 165, 152.

EXAMPLE 3

N-methyl-3-(2-phenanthryl)-acrylohydroxamic acid

Using the procedure of Example 1, but using 2-phenanthrene carboxaldehyde, the desired compound was obtained.
Melting Point: 177°–180° C.
NMR (300 MHz, DMSO-$d_6$): 3.27 (s, 3H); 7.48 (d, 1H); 7.65–8.03 (m, 7H); 8.96 (d, 2H); 9.10 (s, 1H); 10.2 (s, 1H).
Mass Spectrum: 277, 261, 231, 202, 176.

EXAMPLE 4

N-methyl-3-(3-phenanthryl)acrylohydroxamic acid

Using the procedure of Example 1, but using 3-phenanthrene carboxaldehyde, the desired compound was obtained.
Melting Point: 185°–190° C.
NMR (300 MHz, DMSO-$d_6$): 3.27 (s, 3H); 7.45 (d, 1H); 7.65–7.75 (m, 3H); 7.90 (s, 2H); 8.00 (m, 2H); 8.26 (s, 1H); 8.82–8.88 (m, 2H); 10.22 (brs, 1H).
Mass Spectrum: 277, 261, 231, 203.

EXAMPLE 5

N-methyl-3-(9-phenanthryl)-acrylohydroxamic acid

Using the procedure of Example 1, but using 9-phenanthrene carboxaldehyde, the desired compound was obtained.
Melting Point: 170°–173° C.
NMR (300 NHz, DMSO-$d_6$): 3.28 (s, 3H); 7.40 (d, 1H); 7.64–7.79 (m, 4H); 8.09 (d, 1H); 8.21 (m, 2H); 8.28 (d, 2H); 8.85 (d, 1H); 8.92 (d, 1H); 10.24 (s, 1H).
Mass Spectrum: 277, 262, 231, 202.

EXAMPLE 6

N-methyl-3-(2 anthryl)acrylohydroxamic acid

Using the procedure of Example 1, but using 2-anthracene carboxaldehyde the desirred compound was obtained.
Mass Spectrum: 277 (M+), 261, 231, 203

EXAMPLE 7

4-biphenyl hydroxamic acid

Using the procedure of Example 1 part (b), but using 4-biphenyl carboxylic acid and hydroxylamine hydrochloride the desired compound was obtained.
Melting Point: 185°–189° C. (dec).
NMR (300 MHz, DMSO-$d_6$/CDCL$_3$): 7.38 (t, 2H); 7.43 (s, 2H); 7.70 (t, 4H); 7.87 (d, 2H); 8.24 (s, 1H); 9.17 (s, 1H); 11.2 (brs, 1H).
Mass Spectrum: 213, 197, 181, 169, 152.

EXAMPLE 8

3-biphenyl hydroxamic acid

Using the procedure of Example 1 part (b), but using 3-biphenyl carboxylic acid and hydroxylamine hydrochloride, the desired compound was obtained.
Melting Point: 171°–173° C. (dec).
NMR: (300 MHz, DMSO-$d_6$) 7.37–7.60 (m, 4H); 7.70–7.85 (m, 4H); 8.03 (s, 1H); 9.10 (s, 1H); 11.34 (s, 1H).
Mass Spectrum: 213, 197, 181, 152.

EXAMPLE 9

4-(2,4,6-trimethyphenyl)phenyl hydroxamic acid a. Methyl 4-(2,4,6 trimethylphenyl)benzoate Tert-butyl lithium (23 mmole) was added at −78° C. to a THF (15 mL) solution of 2-bromomesitylene (2.3 g, 11.5 mmole). After 15 minutes this solution was transferred via cannula to a suspension of zinc chloride (1.6 g, 11.5 mmole) in THF (10 mL). The resulting mixture was stirred for one hour at room temperature. In a separate flash, di-isobutylaluminum hydride (1.5 mmole) was added to a solution of palladium bis(triphenylphosphino)dichloride (535 mg, 0.76 mmole) in THF (25 mL). To this was added a THF solution (20 mL) of methyl p-iodo benzoate (2.0 g, 7.6 mmole). The zinc reagent prepared above was then added via a cannula to the palladium mixture. After stirring, the reaction was poured into 2N HCl and the product extracted into ether. After evaporation of the ether, the residue was flash chromatographed on 120 g silica gel, eluting with 2% ether in hexanes. A white solid (1.5 g, 52%) was obtained.

NMR (60 MHz): 1.9 (s, 6H); 2.3 (s, 3H); 3.8 (s, 3H); 6.8 (s, 2H); 7.1 (d, 2H); 7.9 (d, 2H).

b. 4-(2,4,6-trimethylphenyl)benzoic acid

The compound from Example 9 part (a) (1.3 g) was dissolved in a mixture of isopropanol (15 mL) and water (8 mL). Lithium hydroxide (1.3 g) was added and the reaction mixture was refluxed. After 2 hours the solution was poured into 2N HCl and the product was extracted into ether. After drying the organic phase with MgSO$_4$ and evaporation a white solid was obtained (1.15 g, 91%).

Mass Spectrum: 240 (M+)

c. 4-(2,4,6-trimethylphenyl)phenyl hydroxamic acid

The desired compound was obtained using the material from Example 9 part (b) and using the procedure of Example 1 part (b), but using hydroxylamine hydrochloride.
Melting Point: 129°–131° C.
NMR (300 MHz, DMSO-$d_6$): 1.92 (s, 6H); 2.27 (s, 3H); 6.95 (s, 4H); 7.2 (d, 2H); 7.83 (d, 2H); 9.1 (brs, 1H); 11.27 (brs, 1H).
Mass Spectrum: 255 (M+), 223, 180.

EXAMPLE 10

4-(1-naphtyl)phenyl hydroxamic acid

Using the procedure of Example 9, but using 1-naphthyl bromide and hydroxylamine hydrochloride the desired material was obtained.

Melting Point: 169°–170° C.
NMR (300 MHz, DMSO-$d_6$): 7.45–8.05 (m, 11H); 9.1 (s, 1H); 11.3 (s, 1H).
IR: (KBr): 1630 (br, s) 3210 (br)
Mass Spectrum: 263 ($M^+$), 231, 202.

EXAMPLE 11

4-(2-naphthyl)phenyl hydroxamic acid

Using the procedure of Example 9, but using 2naphthyl bromide and hydroxylamine hydrochloride. The desired material was obtained.

Melting Point: 190° C. (dec)
NMR (300 MHz, DMSO-$d_6$); 7.5–8.3 (m, 11H); 9.1 (s, 1H); 11.3 (s, 1H).
Mass Spectrum: 263 ($M^+$), 231, 202.

EXAMPLE 12

2-Phenanthrylhydroxamic acid

Using the procedure of Example 1 part (b), but using 2-phenanthrene carboxylic acid and hydroxylamine hydrochloride the desired material was obtained.

Melting Point: 200°–203° C. (dec).
NMR (300 MHz, DMSO-$d_6$): 7.7–8.1 (m, 5H); 8.43 (s, 1H); 8.90 (t, 2H); 9.2 (brs, 1H); 11.45 (s, 1H).
Mass Spectrum: 237, 221, 205, 177, 151.

EXAMPLE 13

3-Phenanthryl hydroxamic acid

Using the procedure of Example 1 part (b), but using 3-phenanthrene carboxylic acid and hydroxylamine hydrochloride, the desired material was obtained.

Melting Point: 180° C. (dec).
NMR (300 MHz, DMSO-$d_6$): 7.65–8.10 (m, 7H); 8.84 (d, 1H); 9.2 (m, 2H); 11.53 (s, 1H).
Mass Spectrum: 237, 221, 205, 203, 193, 177.

EXAMPLE 14

2-Anthrylhydroxamic acid

Using the procedure of Example 1 part (b), but using 2-anthracene carboxylic acid and hydroxylamide hydrochloride, the desired material was obtained.

Melting Point: 185° C. (dec).
NMR (300 MHz, DMSO-$d_6$): 75–8.7 (m, 9H); 10.2 (s, 1H); 11.5 (s, 1H).
Mass Spectrum: 237 ($M^+$), 205, 177.

EXAMPLE 15

5-Lipoxygenase IC$_{50}$ Determination

The compounds of this invention are potent inhibitors of 5-, 12- and 15-lipoxygenase. An assay to determine 5-lipoxygenase activity was performed in incubations containing various concentrations of the test compound and the 20,000 G supernatant from $7.5 \times 10^6$ homogenized RBL-1 cells. Reactions were initiated by the addition of radiolabeled arachidonic acid and terminated by acidification and ether extraction. Reaction products were separated from nonconverted substrate by thin layer chromatography and measured by liquid scintillatiton spectroscopy. Inhibition of 5-lipoxygenase activity was calculated as the ratio of the amounts of product formed in the presence and absence of inhibitor. IC$_{50}$ values were computed as the 50% intercept from linear regression analysis of percentage inhibition versus log concentration plots. Results for compounds of the foregoing Examples are indicated in Table 1, below.

TABLE 1

| Ex. # | R$_1$ | R$_2$ | n | IC$_{50}$uM |
|---|---|---|---|---|
| 1 | 4-biphenyl | CH$_3$ | 1 | 0.13 |
| 2 | 3-biphenyl | CH$_3$ | 1 | 0.071 |
| 4 | 3-phenanthryl | CH$_3$ | 1 | 0.10 |
| 5 | 9-phenanthryl | CH$_3$ | 1 | 0.12 |
| 7 | 4-biphenyl | H | 0 | 4.1 |
| 8 | 3-biphenyl | H | 0 | 6.0 |
| 12 | 2-phenanthryl | H | 0 | 1.9 |
| 13 | 3-phenanthryl | H | 0 | 1.2 |

The inhibitory activities of the compounds of this invention against 12- and 15-lipoxygenase can be determined in the foregoing assay in which 12-lipoxygenase obtained from human platelets, or 15-lipoxygenase obtained from soybean, is substituted for the 5-lipoxygenase-containing cell supernatant fraction. Results of these tests for various of the foregoing compounds are indicated in Table 2.

TABLE 2

| | % Inhibition at Indicated Concentration | | | |
|---|---|---|---|---|
| | 15-lipoxygenase | | 12-lipoxygenase | |
| Ex. # | 100 uM | 10 uM | 100 uM | 10 uM |
| 1 | 74 | 52 | 68 | 63 |
| 2 | 85 | 43 | 96 | 99 |
| 7 | 30 | 0 | 97 | 86 |
| 8 | 33 | 33 | — | — |
| 13 | 39 | 25 | — | — |

What is claimed is:

1. A compound of the formula

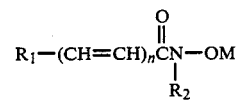

where
R$_1$ is a trinuclear aromatic or biaryl group;
R$_2$ is hydrogen or C$_1$ to C$_6$ alkyl or cycloalkyl; n is 1;
and M is a pharmaceutically acceptable cation.

2. A compound according to claim 1 wherein R$_2$ is C$_1$ to C$_6$ alkyl.

3. A compound according to claim 2 wherein R$_1$ is 3-biphenyl.

4. A compound according to claim 2 wherein R$_1$ is 4-(2,4,6-trimethylphenyl)-phenyl.

5. A compound according to claim 2 wherein R$_1$ is 3-phenanthryl.

6. A compound according to claim 2 wherein R$_1$ is 4-(1-naphthyl)phenyl.

7. A compound according to claim 2 wherein R$_1$ is 4-(2-naphthyl)phenyl.

8. A compound according to claim 1 wherein the pharmaceutically acceptable cation is a nontoxic cation selected from the group consisting of hydrogen, alkali metal cations, alkaline earth metal cations, and ammonium, quaternary ammonium and amine cations.

9. A method of inhibiting lipoxygenase activity in a human or lower animal host in need of such treatment, comprising administering to the human or lower animal host a compound according to claim 1 in an amount effective to inhibit lipoxygenase activity in the host.

10. A method according to claim 9 wherein the compound is administered orally, parenterally, or topically.

11. A method according to claim 10 wherein the compound is administered at a dosage of from 0.001 to 100 mg/kg body weight per day.

12. A method according to claim 11 wherein the compound is administered at a dosage of from 0.01 to 10 mg/kg body weight per day.

13. A composition in unit dosage form for the inhibition of lipoxygenase activity in a human or lower animal host, comprising a compound according to claim 1 and a pharmaceutical carrier material.

* * * * *